United States Patent

Bender et al.

Patent Number: 6,025,536
Date of Patent: Feb. 15, 2000

[54] PROCESS OF MANUFACTURING A COBALT-CHROMIUM ORTHOPAEDIC IMPLANT WITHOUT COVERING DEFECTS IN THE SURFACE OF THE IMPLANT

[75] Inventors: Larry S. Bender, Leesburg; David M. Blakemore; Richard C. Compton, both of Warsaw; Richard B. Cwik, Mishawaka; Leslie N. Gilbertson; Steven M. Humphrey, both of Warsaw; Steven C. Kitch, Akron; Kris K. Merchant, Fort Wayne; Tim A. Mosher; Robin J. Reed, both of Warsaw, all of Ind.

[73] Assignee: Bristol-Myers Squibb Company

[21] Appl. No.: 08/915,296

[22] Filed: Aug. 20, 1997

[51] Int. Cl.⁷ .................................................. A61F 2/28
[52] U.S. Cl. ................................................ 623/16; 623/66
[58] Field of Search ...................... 623/16, 66; 205/322; 266/4 A

[56] References Cited

U.S. PATENT DOCUMENTS

| | | | |
|---|---|---|---|
| 3,730,501 | 5/1973 | Guessier et al. | 266/4 |
| 3,775,180 | 11/1973 | Hirata et al. | 134/7 |
| 4,571,367 | 2/1986 | Yamada et al. | 428/653 |
| 4,718,908 | 1/1988 | Wigginton et al. | 623/16 |
| 4,775,426 | 10/1988 | Murley et al. | 148/2 |
| 5,211,833 | 5/1993 | Shirkhanzadeh | 205/322 |

*Primary Examiner*—David J. Isabella
*Attorney, Agent, or Firm*—Todd A. Dawson

[57] ABSTRACT

An orthopaedic implant is forged from a metallic body consisting of a cobalt-chromium alloy. The forged implant is descaled by blasting the implant with a particulate blasting agent at a momentum which is sufficient to remove scale formed on the implant during the forging step but insufficient to otherwise cause major structural surface deformation to the implant. The descaled implant is electro-chemical polished by submersing the implant in an acid bath having a temperature of between approximately 80° F. and 90° F. The acid bath includes approximately 45% sulfuric acid and 50% phosphoric acid. Direct current electrical power ranging between approximately 10 volts D.C. and 13 volts D.C. is applied to the implant. The polished implant is ultrasonically cleaned. The implant is inspected with a fluorescent penetrant to determine whether surface defects exist in the implant.

23 Claims, 2 Drawing Sheets

PROCESS OF MANUFACTURING A COBALT-CHROMIUM ORTHOPAEDIC IMPLANT WITHOUT COVERING DEFECTS IN THE SURFACE OF THE IMPLANT

BACKGROUND OF THE INVENTION

1. Field of the Invention

The present invention relates to orthopaedic implants, and, more particularly to a method of manufacturing an orthopaedic implant using a post forging process that prevents the covering of surface defects.

2. Description of the Related Art

Orthopaedic implants may be formed using a variety of processes such as milling, casting or forging. It is known to near net forge an orthopaedic implant such that areas of the implant after forging are only slightly larger than the desired finished shape of the implant. Typically, after an implant is near net forged, the implant is exposed to shot peening, grinding or belting techniques to remove scale and excess material. Grinding and belting processes both remove excess material from the implant by abrasive particles which are moved generally parallel to and against the surface of the implant.

Near net forging offers certain advantages in terms of reduced manufacturing costs, predictability and high quality. Moreover, with a near net forging process, very little material must be removed from the implant after forging. This results in decreased manufacturing costs associated with decreased machining. It is, therefore, desirable to use a near net forging process for certain applications of orthopaedic implants.

During the forging process, small surface defects such as cracks or laps may develop in the implant. In a standard forging process, such small surface defects are not critical, as a layer of material containing these cracks or defects will be removed. However, in a near net forging operation, as discussed, only a small amount of material is removed by shot peening, grinding and belting. As these processes are intended only to remove a small layer of material in a near net process, in some circumstances, the crack or defect may not be removed. In fact, a problem with shot peening, grinding and belting is that a portion of the crack at the surface of the implant may be covered or smeared during the machining process. A fragmentary, enlarged cross-sectioned portion of a metallic test specimen having a surface crack covered during a shot peening process is illustrated in FIG. 1. The illustration of FIG. 1 is illustrative of the problems that may be experience when forming an implant using the current technology for removing scale and extra material from a near net forged implant. The implant may be inspected with a fluorescent penetrant to detect the presence of such surface defects. However, if the crack is covered or masked (See FIG. 1) using a shot peening, grinding or belting process, the fluorescent penetrant will not penetrate into the crack such that the crack may be detected. This of course means that when the crack is covered or masked, the implant may have a subsurface discontinuity which is not detected or removed during the manufacturing process.

What is needed in the art is a method of manufacturing an orthopaedic implant using a near net forging technique which allows the implant to be finished without covering or masking the presence of surface defects such as cracks.

SUMMARY OF THE INVENTION

The present invention provides a method of more accurately determining whether surface defects exist in a cobalt-chromium orthopaedic implant formed by near net forging and subsequent finishing.

The invention comprises, in one form thereof, a process of manufacturing an orthopaedic implant. The implant is forged from a metallic body consisting of a cobalt-chromium alloy or a stainless steel alloy. The forged implant is descaled by blasting the implant with a particulate blasting agent at a momentum which is sufficient to remove scale formed on the implant during the forging step but insufficient to otherwise cause structural surface deformation to the implant. The descaled implant is ultrasonically cleaned. The descaled and ultrasonically cleaned implant is electrochemically polished by submersing the implant in an acid bath having a temperature of between approximately 80° F. and 90° F. The acid bath includes approximately 45% sulfuric acid and 50% phosphoric acid. Direct current electrical power ranging between approximately 10 volts D.C. and 13 volts D.C. is applied to the implant. The electrochemically polished implant is ultrasonically cleaned. The implant is inspected with a Level III penetrant to determine whether surface defects exist in the implant.

An advantage of the present invention is that an orthopaedic implant can be formed using near net forging and minimal subsequent machining, without covering or masking surface defects in the implant and allowing detection of those unmasked defects by penetrant inspection.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 2:
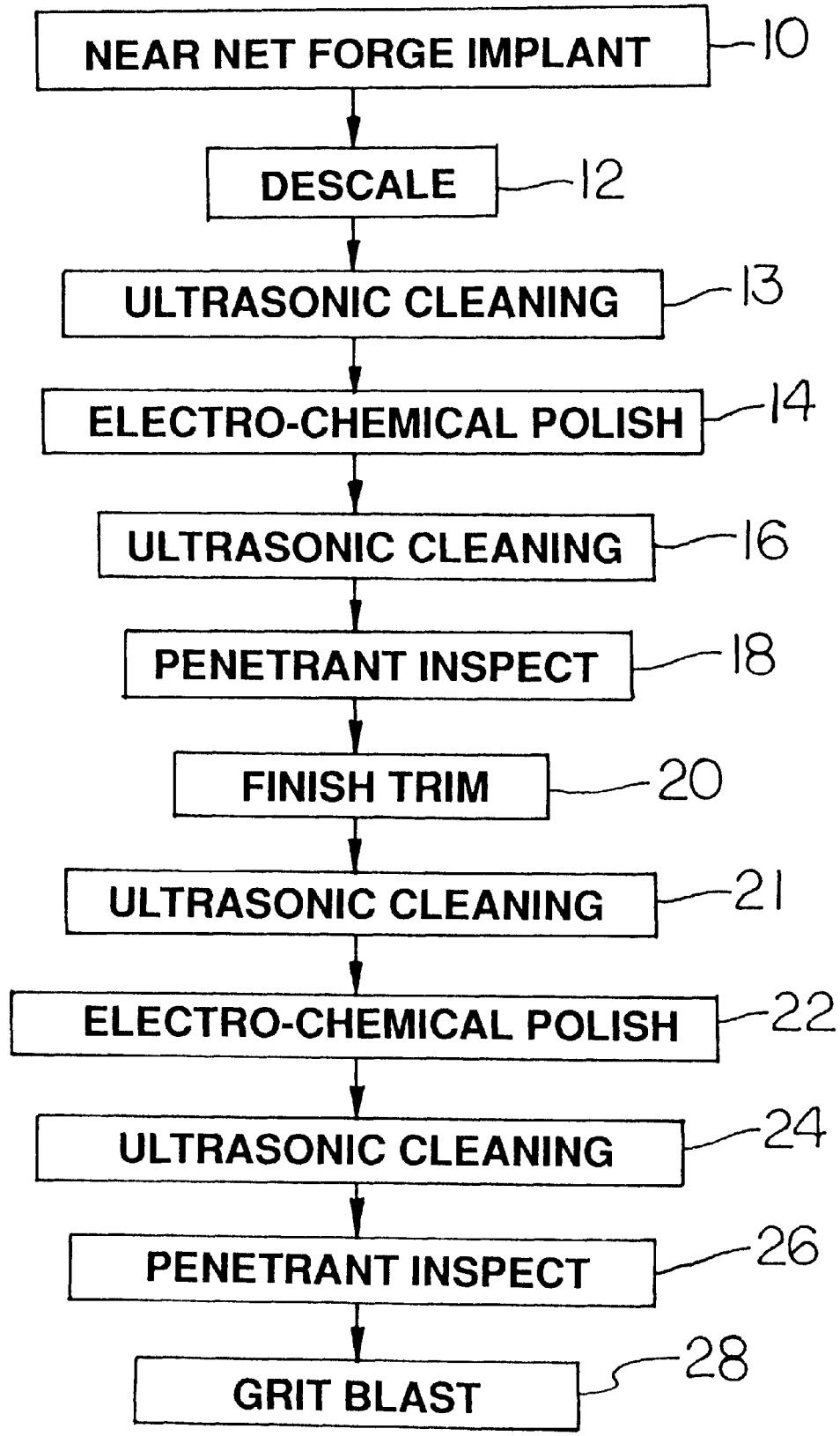
FIG. 2 is a flow chart which illustrates one embodiment of the process of the present invention for manufacturing an orthopaedic implant.

Referring now to the drawings, and particularly to FIG. 2, there is shown a flow chart which illustrates one embodiment of the process of the present invention for manufacturing an orthopaedic implant, such as a hip stem implant. The process of the present invention allows an orthopaedic implant to be formed using a near-net forged technique, thereby utilizing advantages associated with near net forging. At the same time, the process machines and finishes the near net forged implant in a manner such that surface defects, such as cracks, laps, etc., can still be detected using a fluorescent penetrant inspection technique.

Figure 1:
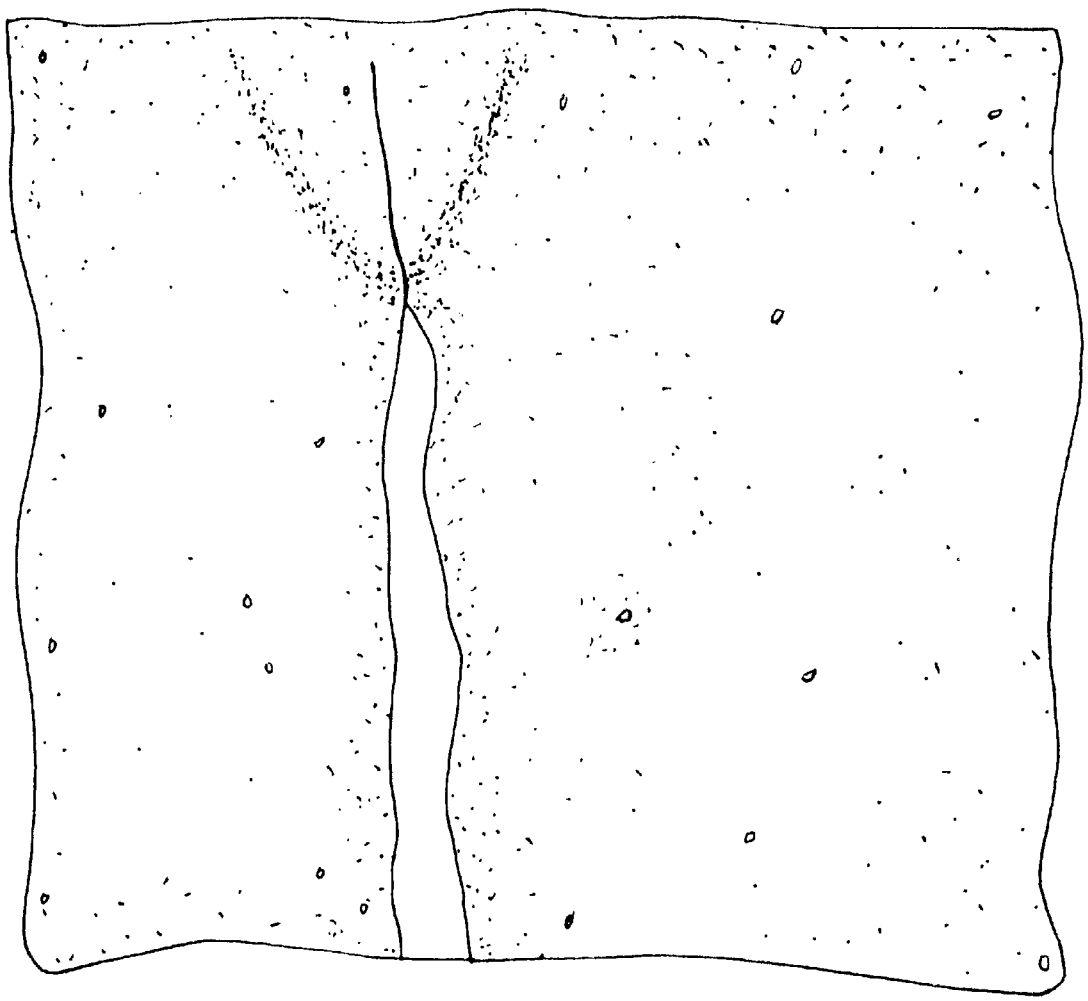
FIG. 1 is an enlarged, fragmentary view of a portion of a metallic test specimen showing a crack which has been closed at the surface of the implant using conventional manufacturing techniques.

A metallic body consisting essentially of a cobalt-chromium alloy is forged using conventional forging techniques to a near net shape defining the orthopaedic implant (block 10). The near net forged orthopaedic implant may or may not include surface defects such as the surface crack shown in FIG. 1 (but of course not covered since the surface is not excessively deformed by aggressive descaling or machining techniques). The term "near net", as used in this application, is intended to mean that the orthopaedic implant is forged to a shape which closely approximates the final shape of the implant. That is, only minimal machining is required subsequent to the forging. For example, the orthopaedic implant may be forged such that only several thousandths of an inch of material in the flash regions is required to be removed from the forged implant.

During the forging process, scale forms on the cobalt-chromium implant as a result of the elevated temperature at which the forging is carried out. It is thus necessary to descale the forged implant to remove the scale therefrom (block 12). Conventional machining techniques used to remove scale from a near net forged body cannot be used since such processes also deform the surface of the implant and may hide surface defects. For example, shot peening and belting with an abrasive grit tend to cover or mask surface defects such as cracks in an orthopaedic implant. (See FIG. 1).

In contrast with conventional descaling techniques, the present invention utilizes a descaling technique which blasts the implant with a particulate blasting agent at a momentum which is sufficient to remove scale formed on the implant during the forging step, but insufficient to otherwise cause structural surface deformation to the implant. In other words, the blasting agent particulates are selected with a particular mass and are blasted against the implant at a selected velocity such that the resultant momentum of the blasting agent particulate does not cause significant surface deformation to the implant. Surface deformation would be considered significant if a crack or defect is closed to a depth of material that would not be removed during the electro-chemical machining process described below.

In one embodiment of the present invention, the implant is descaled by blasting the implant with glass beads having a mesh size of between approximately 170 to 325 mesh from a nozzle having an inside diameter of approximately 0.360 inch. The operating pressure of the glass bead blasting agent is maintained at less than 100 lbs per square inch, in order to assure that surface defects are not covered or masked on the implant.

In another embodiment of the method of the present invention, the implant is descaled by blasting the implant with 220 grit aluminum-oxide from a nozzle having an inside diameter of approximately 0.259 inch and an operating pressure of approximately 60 lbs per square inch (PSI).

In yet another embodiment of the method of the present invention, the implant is descaled by blasting the implant with 90 grit aluminum-oxide from a nozzle having an inside diameter of approximately 0.295 inch and an operating pressure of approximately 40 PSI.

For each of the three above-described methods of descaling the implant, the mass of the blasting agent particulates and the velocity (corresponding to the operating pressure) at which the particulates impinge upon the implant is selected such that scale is removed while surface deformation does not occur. Of course, it will be appreciated that other blasting agents having particulates with appropriately sized masses which impinge upon the implant at selected velocities may also be selected. The important criteria is that the scale is removed, while surface defects such as cracks are not covered or masked.

After the implant is descaled, the implant is then preferably ultrasonically cleaned (block 13). More particularly, the implant is placed within a solution of water and detergent having an operating temperature of between approximately 120° F. and 150° F. The implant is cleaned with ultrasonic energy for a period of around ten minutes.

After descaling and cleaning, the implant is electrochemical polished using an electrolytic solution and direct current electrical power (block 14). The electrochemical polishing accomplishes two primary purposes. First, a predetermined depth layer may be removed from the surface of the implant by electrochemical machining. Secondly, the electrochemical polishing provides a high luster finish to the cobalt-chromium alloy which may be desirable for engineering and/or marketing purposes.

In the embodiment shown, the electro-chemical polishing is carried out by submersing the implant in an acid bath having a temperature of between approximately 80° F. and 150° F., preferably between 80° F. and 90° F., and more preferably approximately 86° F. The acid bath includes, e.g., approximately 45% sulfuric acid, 50% phosphoric acid, and a 5% buffer. After the implant is submerged in the acid bath, a direct current electrical power is applied to the implant. More particularly, the implant is submerged within a container (not shown) which contains the acid bath. The container, or other structural support associated with the container, is connected to the source of direct current electrical power as a cathode and the implant is connected to the source of direct current electrical power as an anode. The acid bath carries ions between the anode and the cathode during the electro-chemical polishing process. In the embodiment shown, the direct current electrical power ranges between 10 volts DC and 13 volts DC, preferably ranges between 11.4 volts DC and 11.7 volts DC, and more preferably is approximately 11.7 volts DC. In the preferred embodiment the current density used during the electro-chemical polishing process is 2 amperes per square inch to remove approximately 0.001 of an inch of material during a 180 second period. Again, it is preferable to have an approximate 15 second dwell time between each 45 second period when the current is turned on.

After the implant is electro-chemically polished, the implant is then ultrasonically cleaned (block 16). More particularly, the implant is placed within a solution of water and detergent having an operating temperature of between approximately 120° F. and 150° F. The implant is cleaned with ultrasonic energy for a period of around ten minutes.

The implant is then inspected using a penetrant to determine whether surface defects such as cracks exist within the implant (block 18). The existence of such surface defects may necessitate further processing of the implant to ensure that the surface defects are removed. In the embodiment shown, the fluorescent penetrant is a water soluble fluorescent penetrant, level III. Such a penetrant works at least in part on the principal of capillary action such that the penetrant is at least partially absorbed into open surface defects such as cracks. A fluorescent penetrant of this type is sold by Magnaflux in Chicago, Ill., U.S.A.

After the implant is inspected for surface defects using the fluorescent penetrant, the flashing on the implant is trimmed (block 20). The flashing in general is in the form of small pieces of metal which extend from the implant at the location where the dies used during the forging mate with each other. The flashing must of course be trimmed off subsequent to the forging process.

After the implant is finish trimmed to remove the flashing, the implant is again ultrasonically cleaned (block 21), electro-chemically polished (block 22) and ultrasonically cleaned (block 24) again and inspected using a fluorescent penetrant (block 26). The electro-chemical polishing, ultrasonic cleaning and fluorescent penetrant inspection methods used in blocks 21, 22, 24 and 26 are identical to those used in blocks 13, 14, 16 and 18, and thus will not be described in further detail.

After the implant is inspected using a fluorescent penetrant for the second time (block 26), the implant is essentially in a finished state. The manufacturing steps carried out in the sequence described above ensure that any surface defects in the implant will be detected and not hidden. The near net forging, descaling using a low energy blasting media, electro-chemical polishing under the specified conditions, and ultrasonic cleaning ensure that surface defects in the implant will be detected during the manufacture of the implant.

After the implant has been manufactured and inspected using the manufacturing processes set forth in blocks 10–26, the implant may optionally be provided with a roughened or textured finish by grit blasting selected portions of the implant, such as the stem portion (block 28). In contrast with the blasting technique of the present invention carried out in block 12, the grit blast carried out in block 26 is more akin to conventional blasting techniques. To wit, the implant is grit blasted such that the mass and velocity of the particles of the blasting agent result in a momentum which is sufficient to deform a portion of the surface of the implant. The surface of the implant may thus be roughened, textured or otherwise machined using such a grit blast.

In the embodiment shown in FIG. 2, the flashing is trimmed from the implant after the implant is electro-chemically polished, ultrasonically cleaned (before and after polishing) and inspected with a fluorescent penetrant. However, it will also be appreciated that it may be possible or desirable to finish trim the flashing from the implant either immediately before or after the implant is descaled (i.e., between blocks 10 and 12 or between blocks 12 and 14). If the finish trim operation is carried out before or after the descale operation, the additional electro-chemical polishing, ultrasonic cleaning and fluorescent inspection steps carried out in blocks 22, 24 and 26 may not be necessary. That is, it may be possible to combine the electro-chemical polishing step of block 22 with the electro-chemical polishing step of block 14; combine the ultrasonic cleaning step of block 24 with the ultrasonic cleaning step of block 16; and combine the fluorescent penetrant inspection step of block 26 with the fluorescent penetrant inspection step of block 18.

It should be understood that while the invention has been described for use in manufacturing an implant from a cobalt-chromium alloy, such should not be considered a limitation. The principles of the invention apply equally to an implant formed from any other acceptable material. However, as would be readably understood by one skilled in the art, the electro-chemical polishing parameters would need to be adjusted to accommodate a change of material.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant manufactured by a process including the sequential steps of:
    forging the implant from a metallic body comprised of a cobalt-chromium alloy;
    descaling the forged implant by impingement of the implant with a particulate agent at a momentum and time which is sufficient to remove scale formed on the implant during said forging step but insufficient to otherwise cause significant surface deformation to the implant;
    electro-chemical milling the descaled implant, said electro-chemical milling step including the substeps of:
        submersing the implant in an acid bath having a temperature of between approximately 80° F. and 90° F., said acid bath including approximately 45% sulfuric acid and 50% phosphoric acid; and
        applying direct current electrical power to the implant, said direct current electrical power ranging between approximately 10 volts D.C. and 13 volts D.C.;
    ultrasonically cleaning the polished implant; and
    inspecting the implant with a penetrant to determine whether surface defects exist in the implant.

2. The process of manufacturing an orthopaedic implant of claim 1, wherein said direct current electrical power applied to the implant ranges between approximately 11.4 volts D.C. and 11.7 volts D.C.

3. The process of manufacturing an orthopaedic implant of claim 2, wherein said direct current electrical power applied to the implant ranges is approximately 11.7 volts D.C.

4. The process of manufacturing an orthopaedic implant of claim 3, wherein said acid bath has a temperature of approximately 86° F.

5. The process of manufacturing an orthopaedic implant of claim 1 wherein said direct current electrical power applied to the implant is approximately 2 amps per square inch.

6. The process of manufacturing an orthopaedic implant of claim 1, wherein said descaling step comprises blasting the implant with glass beads having a mesh size of between approximately 170–325 mesh from a nozzle having an inside diameter of approximately 0.360 inch and at a pressure of less than 100 pounds per square inch.

7. The process of manufacturing an orthopaedic implant of claim 1, wherein said descaling step comprises blasting the implant with 220 grit aluminum-oxide from a nozzle having an inside diameter of approximately 0.295 inch and at a pressure of approximately 60 pounds per square inch.

8. The process of manufacturing an orthopaedic implant of claim 1, wherein said descaling step comprises blasting the implant with 90 grit aluminum-oxide from a nozzle having an inside diameter of approximately 0.295 inch and at a pressure of approximately 40 pounds per square inch.

9. The process of manufacturing an orthopaedic implant of claim 1, comprising the further sequential steps of:
    trimming flashing from the implant, said flashing being formed on the implant during said forging step;
    electro-chemical polishing the trimmed implant, said electro-chemical polishing step including the substeps of:
        submersing the implant in an acid bath having a temperature of between approximately 80° F. and 90° F., said acid bath including approximately 45% sulfuric acid and 50% phosphoric acid; and
        applying direct current electrical power to the implant, said direct current electrical power ranging between approximately 10 volts D.C. and 13 volts D.C.;

ultrasonically cleaning the polished implant; and inspecting the implant with a fluorescent penetrant to determine whether surface defects exist in the implant.

10. An orthopaedic implant manufactured by a process including the sequential steps of:

forging the implant from a metallic body;

descaling the forged implant by impingement of the implant with a particulate agent at a momentum which is sufficient to remove scale formed on the implant during said forging step but insufficient to otherwise cause significant surface deformation to the implant;

electro-chemical polishing the descaled implant, said electro-chemical polishing step including the substeps of submersing the implant in an electrolytic solution and applying direct current electrical power to the implant, wherein said electrolytic solution comprises an acid bath including approximately 45% sulfuric acid and 50% phosphoric acid; and inspecting the implant with a fluorescent penetrant to determine whether surface defects exist in the implant.

11. The process of manufacturing an orthopaedic implant of claim 10, wherein said acid bath has a temperature of between approximately 80° F. and 150° F.

12. The process of manufacturing an orthopaedic implant of claim 10, wherein said acid bath has a temperature of between approximately 80° F. and 90° F.

13. The process of manufacturing an orthopaedic implant of claim 12, wherein said acid bath has a temperature of approximately 86° F.

14. The process of manufacturing an orthopaedic implant of claim 10, wherein said direct current electrical power applied to the implant ranges between approximately 10 volts D.C. and 13 volts D.C.

15. The process of manufacturing an orthopaedic implant of claim 14, wherein said direct current electrical power applied to the implant ranges between approximately 11.4 volts D.C. and 11.7 volts D.C.

16. The process of manufacturing an orthopaedic implant of claim 15, wherein said direct current electrical power applied to the implant ranges is approximately 11.7 volts D.C.

17. The process of manufacturing an orthopaedic implant of claim 10, wherein said descaling step comprises blasting the implant with glass beads having a mesh size of between approximately 170–325 mesh from a nozzle having an inside diameter of approximately 0.360 inch and at a pressure of less than 100 pounds per square inch.

18. The process of manufacturing an orthopaedic implant of claim 10, wherein said descaling step comprises blasting the implant with 220 grit aluminum-oxide from a nozzle having an inside diameter of approximately 0.295 inch and at a pressure of approximately 60 pounds per square inch.

19. The process of manufacturing an orthopaedic implant of claim 10, wherein said descaling step comprises blasting the implant with 90 grit aluminum-oxide from a nozzle having an inside diameter of approximately 0.295 inch and at a pressure of approximately 40 pounds per square inch.

20. The process of manufacturing an orthopaedic implant of claim 10, comprising the further sequential steps of:

trimming flashing from the implant, said flashing being formed on the implant during said forging step;

electro-chemical polishing the descaled implant, said electro-chemical polishing step including the substeps of:

submersing the implant in an acid bath having a temperature of between approximately 80° F. and 90° F., said acid bath including approximately 45% sulfuric acid and 50% phosphoric acid; and applying direct current electrical power to the implant, said direct current electrical power ranging between approximately 10 volts D.C. and 13 volts D.C.;

ultrasonically cleaning the polished implant; and inspecting the implant with a fluorescent penetrant to determine whether surface defects exist in the implant.

21. The process of manufacturing an orthopaedic implant of claim 10, comprising the further sequential step of blasting the implant with a blasting agent at a momentum which is sufficient to remove scale from the implant and abrade a portion of the implant.

22. The process of claim 10 wherein said metallic body is formed from a cobalt chrome alloy.

23. An orthopaedic implant manufactured by a process including the steps of:

forming the implant from a metallic body comprised of a cobalt-chromium alloy;

electro-chemical polishing the implant, said electro-chemical polishing step including the substeps of:

submersing the implant in an acid bath having a temperature of between approximately 80° and 90° F., said acid bath including approximately 45% sulfuric acid and 50% phosphoric acid; and applying direct current electrical power to the implant, said direct current electrical power ranging between approximately 10 volts D.C. and 13 volts D.C.

* * * * *